US012740899B2

(12) United States Patent
Lees et al.

(10) Patent No.: US 12,740,899 B2
(45) Date of Patent: Sep. 22, 2026

(54) PERSONAL HYGIENE PRODUCT

(71) Applicant: Croda International Plc, Goole (GB)

(72) Inventors: Suzanne Burn Lees, Goole (GB); Ross Sellars, Goole (GB); Ryan Michael McDonald, Goole (GB)

(73) Assignee: Croda International Plc, Goole (GB)

( * ) Notice: Subject to any disclaimer, the term of this patent is extended or adjusted under 35 U.S.C. 154(b) by 636 days.

(21) Appl. No.: 17/634,378

(22) PCT Filed: Aug. 11, 2020

(86) PCT No.: PCT/EP2020/072456
§ 371 (c)(1),
(2) Date: Feb. 10, 2022

(87) PCT Pub. No.: WO2021/028415
PCT Pub. Date: Feb. 18, 2021

(65) Prior Publication Data

US 2022/0323269 A1 Oct. 13, 2022

(30) Foreign Application Priority Data

Aug. 13, 2019 (GB) ..................................... 1911568

(51) Int. Cl.
*A61F 13/511* (2006.01)
*A61F 13/514* (2006.01)
(Continued)

(52) U.S. Cl.
CPC ......... *A61F 13/51113* (2013.01); *A61L 15/20* (2013.01); *A61L 15/28* (2013.01);
(Continued)

(58) Field of Classification Search
CPC ...... A61F 13/51113; A61F 2013/51117; A61F 2013/51411; A61L 2300/216; A61L 15/20; A61L 15/28; A61L 15/44
See application file for complete search history.

(56) References Cited

U.S. PATENT DOCUMENTS

2003/0114520 A1* 6/2003 Pereira ..................... A61K 8/86
514/532
2004/0242097 A1* 12/2004 Hasenoehrl ........ A44B 18/0011
442/361
(Continued)

FOREIGN PATENT DOCUMENTS

CN 107647971 A 2/2018
EP 1371379 A1 12/2003
(Continued)

OTHER PUBLICATIONS

"Cromollient SCE (Di-PPG-2 Myreth-10 Adipate)", humblebee & me, https://www.humblebeeandme.com/project/cromollient-sce/, downloaded from the internet Feb. 1, 2022, 6 pages.
(Continued)

*Primary Examiner* — Jessica Arble
(74) *Attorney, Agent, or Firm* — Buchanan Ingersoll & Rooney PC

(57) ABSTRACT

The present invention relates to skin care additive which comprises a diester skin care additive which is the reaction product of a fatty alkoxylated ester and a straight, branched or aromatic polyol or poly acid, where the skin care additive provides improved wet lubricancy and/or reduced skin irritancy. More especially, there is provided a personal hygiene product treated with the skin care additive, as such the invention also relates to providing the care additive as a coating on a personal hygiene product. The present invention may also provide use of such a personal hygiene product
(Continued)

comprising said skin care additive to prevent or alleviate dermatitis, and in particular nappy rash.

17 Claims, 7 Drawing Sheets

(51) Int. Cl.
*A61L 15/20* (2006.01)
*A61L 15/28* (2006.01)
*A61L 15/44* (2006.01)

(52) U.S. Cl.
CPC ..... *A61L 15/44* (2013.01); *A61F 2013/51117* (2013.01); *A61F 2013/51411* (2013.01); *A61L 2300/216* (2013.01)

(56) References Cited

U.S. PATENT DOCUMENTS

| | | | | |
|---|---|---|---|---|
| 2008/0200894 | A1* | 8/2008 | Gatto | A61F 13/15 604/385.01 |
| 2013/0337710 | A1* | 12/2013 | Rocafort | D06M 15/00 442/102 |
| 2014/0236072 | A1* | 8/2014 | Zhang | A61M 1/06 604/23 |
| 2016/0331604 | A1* | 11/2016 | Hao | A61F 13/84 |
| 2016/0354506 | A1* | 12/2016 | Chmielewski | B32B 5/022 |
| 2017/0246052 | A1* | 8/2017 | Ludwig | A61F 13/15585 |

FOREIGN PATENT DOCUMENTS

| | | | |
|---|---|---|---|
| JP | 2003206499 | A | 7/2003 |
| JP | 2005-511493 | A | 4/2005 |
| JP | 2005-528971 | A | 9/2005 |
| JP | 2006520324 | A | 9/2006 |
| JP | 2017012319 | A | 1/2017 |
| JP | 2019025148 | A | 2/2019 |
| WO | 9616681 | A1 | 6/1996 |
| WO | 03/013439 | A2 | 2/2003 |
| WO | 03105916 | A1 | 12/2003 |

OTHER PUBLICATIONS

International Search Report and Written Opinion for International Application No. PCT/EP2020/072456, dated Oct. 20, 2020, 10 pages.

Great Britain Search Report for Great Britain Application No. GB1911568.2, dated Jan. 17, 2020, 3 pages.

Fallon et al., “An experimental study of friction between volar forearm skin and nonwoven fabrics used in disposable absorbent products for incontinence”, Proc IMechE Part H: J Engineering in Medicine, 2018: E-ISSN:2041-3033, Journal Code 8908934, pp. 1-13.

Office Action (Notification of Reasons for Refusal) issued Sep. 24, 2024, by the Japanese Patent Office in corresponding Japanese Patent Application No. 2022-508565 with an English translation of the Office Action. (7 pages).

* cited by examiner

PERSONAL HYGIENE PRODUCT

CROSS-REFERENCE TO RELATED APPLICATIONS

This application is a U.S. National Phase application of PCT International Application No. PCT/EP2020/072456, filed Aug. 11, 2020, which claims the benefit of GB Application No. 1911568.2, filed Aug. 13, 2019, both of which are incorporated by reference herein in their entireties.

The present invention relates to a personal hygiene product comprising at least a first layer having a top surface and a bottom surface, and a second layer having a top surface and a bottom surface, wherein at least said first layer comprises a diester skin care additive which is the reaction product of a fatty alkoxylated ester and a straight, branched or aromatic polyol or poly acid. The skin care additive provides improved wet lubricancy and/or reduced skin irritancy. The invention also relates to providing the care additive as a coating on a personal hygiene product. The present invention also provides use of such a personal hygiene product comprising skin care additive to prevent or alleviate dermatitis, and in particular nappy rash.

Personal hygiene products of all sorts have been growing in popularity and type since the late $19^{th}$ century, and consumers now have a large degree of choice in terms of cost and quality of personal hygiene products which are available on the market. Such products are used in direct contact with a person's skin, and often used in direct contact with delicate and sensitive skin areas or sensitive skin types.

Skin discomfort, damage and infection, as a result of abrasion, dermatitis etc., arising from (or contributed to by) use of personal hygiene products is well known and documented. The stick and slip behaviour of the materials used to make up personal care hygiene products is known to be a contributing factor to user discomfort and skin damage (see Proc IMechE Part H: J Engineering in Medicine, p. 1-13, 2018: E-ISSN: 2041-3033, Journal Code 8908934). One area of wide spread technical interest is avoidance or alleviation of dermatitis caused by wearing incontinence diapers (commonly referred to as diaper rash); this is a problem experienced by both babies and elderly adults who tend to have thinner more sensitive skin. Many solutions to the problem of this type of dermatitis have been suggested including, for example, providing the diaper with an anti-bacterial agent (Chinese patent publication CN107647971), providing a low friction material as the skin contact textile layer (Japanese patent publication JP2019025148) and providing a skin contact textile layer with physical means to reduce the amount of water in contact with the skin (Japanese patent publication JP2017012319).

The provision of balms and lotions to facial tissues to increase user comfort has also gained popularity in recent years. Such facial tissue products are particularly beneficial for use when users are afflicted with cold and flu viruses and their symptoms include a runny nose. The increase in nose wiping to deal with the increase in mucus produced by the nose often causes the skin around the nasal passages to become damaged, the damage to the skin is aggravated by the rough nature of the facial tissue material.

More especially, increase in friction caused due to fabric products becoming wet is a common contributing factor to skin irritation experienced when using personal hygiene products. This wet friction is particularly a problem when the skin contact layer of the personal hygiene product is made from a nonwoven fabric. The reduction in the wet friction between skin and the personal hygiene product (nonwoven) fabric in contact with the skin is an option to aid in reducing irritation from nonwoven products. However, particularly in relation to diapers some skin irritation is inevitable from sources such as surfactants and prolonged contact with urine; the inclusion of a counter-irritant can help to lessen the irritation from these factors. The body's natural reaction to irritation is to increase blood flow to irritated areas, causing inflammation and so blood flow can be assessed as an indicator of irritation.

The present invention seeks to provide a skin care additive which may find utility in personal hygiene products so that the problems highlighted above may be avoided or alleviated. The present invention finds particular utility in absorbent personal hygiene products where such problems are commonly experienced by end users of such products but may also be useful in non-absorbent products as discussed below.

Accordingly, the present invention provides a personal hygiene product, as claimed herein, comprising:

at least a first layer having a top surface and a bottom surface, wherein at least said first layer comprises a skin care additive, and characterised in that said skin care additive is a diester which is the reaction product of a fatty alkoxylated ester and a straight, branched or aromatic polyol or poly acid.

Methods of providing the skin care additive as a coating on at least the top surface of the at least first layer are also contemplated.

The present invention further provides use of a personal hygiene product according to the first aspect of the present invention to prevent or alleviate dermatitis.

Alternatively, the invention may be understood to provide a method of preventing, or treating, dermatitis by use of the personal hygiene product according to the first aspect of the present invention.

As such, in accordance with the first embodiment of the present invention there is provided a personal hygiene product, comprising:

at least a first layer having a top surface and a bottom surface, wherein at least said first layer comprises a skin care additive, and characterised in that said skin care additive is a diester which is the reaction product of a fatty alkoxylated ester and a straight, branched or aromatic polyol or poly acid.

Preferably, the personal hygiene product also comprises at least a second layer having a top surface and a bottom surface.

Each of the layers of the personal care product can be considered to have a laminar structure, arranged in close proximity to each other to produce the overall product form. Where the product comprises a first layer and a second layer, these layers may be provided in contact with one another, or they may be separated by a further layer interposed between the first and second layers. The first and second layers can be conveniently considered to have a bottom surface and a top surface, and in this case the top surface is considered to be the skin/air contact surface, and the bottom surface is the surface which is internal to the product (i.e. in contact with the bottom surface of the other layer, or in contact with a further layer when present).

More especially, the personal hygiene product may be formed of many layers, more especially, three, four or five layers in total (including said first and second layer). In this case, the first layer top surface should be understood to the external skin contact layer when the product is in use, the bottom surface of the first layer being in contact with either the bottom surface of the second layer, or alternatively spaced from the bottom surface of the second layer by one or more further layers if present. The second layer top surface should be understood to be the opposing external surface of the personal hygiene product, in the case of for example a wipe, this second layer top surface may also be intended as skin contact surface, or alternatively, in the case of for example a diaper or pad, this top surface may be intended for contact with clothing and in particular underwear. The bottom surface of both the first and second layer can be understood as internal to the personal hygiene product when at least two layers are present. Such an arrangement of layers will be well understood by the person skilled in the art.

In accordance with the present invention, the skin care additive provides improved wet lubricancy or reduced skin irritancy, and preferably both such that the skin care additive is a dual function additive; such an additive offers skin care benefits to a user when the personal hygiene product is in use. As will be appreciated by the skilled person in the art, and as further described below, the personal hygiene product may suitably comprise additional optional active additives which could also be considered to provide a skin care benefit, as such skin moisturisation or skin cooling effects, and to avoid any confusion with such a skin care additive the skin care additive of the present invention may conveniently be referred to as the "diester skin care additive" in the present description.

The personal hygiene product may suitably be a tissue, a wipe, a diaper, a pad, a feminine care product, or a face mask. A tissue may include facial or toilet tissues. A wipe may include baby wipes, toddler wipes, sterilisation wipes, hand wipes (particularly antibacterial hand wipes), facial or body wipes (sometimes referred to as shower wipes). A diaper may include e.g. incontinence diapers for babies, adults, or children in the form of tab closure diapers, pull up pants (typical used for toddler potty training and young children with incontinence) or underwear (typically used for older children and adults with incontinence). Pads may include, e.g. breast feeding nursing pads, bed pads, incontinence pads for both children and adults, and sanitary pads. A feminine care product may include e.g. sanitary pads and tampons. Typically, personal hygiene products comprise at least a first and at least a second layer, however, wipes often preferably consist of a first layer only; this may preferably be the case where the wipes have been designed to be suitable for flushing as a means of disposal as minimising the bulk of the overall product allows such products to be flushed with relative ease, and may also allow the products to break down more quickly once flushed to avoid undesirable blockages occurring in sanitation systems.

It will of course be appreciated that the application of the skin care additive may also find utility in medical products such as, for example, bed sore cushions, and wound management products including closing strips, wound dressings, and the like. However, such medical products do not fall within the scope of the invention as claimed herein, which is limited to personal hygiene products.

Preferably, the personal hygiene product further comprises at least one absorbent layer which is interposed between said first layer and said second layer, such that the personal hygiene product is an absorbent hygiene product. The problem of dermatitis may be exacerbated in situations where a user's skin is in prolonged contact with moisture, as is the case during use of absorbent hygiene products; as such provision of a skin care additive of the sort described herein has particular advantages when provided to an absorbent hygiene product. Suitably, the absorbent hygiene product may be: a diaper, a pad, or a feminine care product. Preferably the absorbent hygiene product is a diaper.

Preferably, the diester skin care additive comprises of two fatty alkoxylated moieties of the structure (I):

(I)

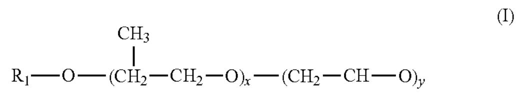

wherein:

$R_1$ is a saturated or unsaturated, substituted or unsubstituted, straight, branched, or aromatic fatty acid moiety having a carbon chain length of from about 6 to about 30 atoms; and Each x and y are independently zero or an integer from 1 to 200, with the proviso that the sum of x and y in each fatty alkoxylated moiety is independently between 1 and 300, and the sum of all xs and ys in the diester does not exceed 800.

More preferably, the diester skin care additive comprises a straight, branched, or aromatic polyol or polyacid of the formula (II):

(II)

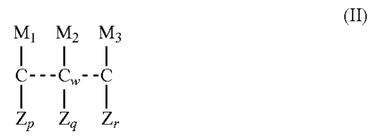

wherein:

$M_1$, $M_2$, and $M_3$ are independently a hydroxy, two single bonded hydrogens, or a double bonded oxygen;

$Z_p$, $Z_q$, and $Z_r$ are independently hydrogen or a hydroxy;

p, q, and r are independently zero or one, with the proviso that the sum of p+q+r is at least 2; and w is zero or an integer between 1 and 20.

More preferably the diester skin care additive comprises an alkoxylated di-ester of myristyl alcohol and adipic acid. Most preferably the diester skin care additive is di-PPG-2 myreth-10 adipate.

As will be understood by the skilled person treat rate is a term of art, and treat rate weight % is calculated on the basis of the weight of the layer of interest to which the additive is incorporated or applied (i.e. relative to the layer treated with the additive)—it is not calculated as a percentage by weight of the total hygiene product weight.

Suitably, the personal hygiene product comprises said diester skin care additive at a treat rate of at least 0.5 weight %. A treat rate of below 0.5 weight % is less preferred, although this treat rate may still provide skin care benefits if formulated in combination with alternative/additional active additives such as antimicrobial agents. However, it is preferred that the diester skin care additive be used as the sole active skin care additive for reasons of cost and time in formulating, and also simplicity of formulating since the potential interactions between multiple active components does not need to be considered.

Preferably, the personal hygiene product comprises said diester skin care additive at a treat rate of less than 5 weight %. No additional skin care benefit has been observed at treat rates above this weight %.

More preferably, the personal hygiene product comprises said diester skin care additive at a treat rate of between 0.5 weight % and 3.0 weight %, and most preferably at a treat rate of between 0.75 weight % and 2.5 weight %. Ideally, the personal hygiene product comprises said diester skin care additive at a treat rate of between about 1 weight % and about 2 weight %. Such a treat rate has been found to provide the optimum balance between providing improved wet lubricancy and reduced skin irritancy skin care benefits, and this treat rate is particularly well suited to absorbent hygiene products, and more especially diapers.

By measuring trans-epidermal water loss (TEWL) the relative skin condition for an individual can be determined. Damaged skin loses some ability to regulate water loss, resulting in increased water loss across the skin barrier. As such, TEWL is a convenient means by which the efficacy of the present diester skin care additive can be evaluated.

As alluded to above, suitably, the personal hygiene product may further comprise an additional additive. Such an additional additive may be selected from one or more of the following additives: known hygiene finishes, lanolin, botanicals, phase change materials, and emollients amongst others. The presence of additional additives will depend upon the type of personal hygiene product and suitable additional additives may be known to the skilled person in the art. For example, the inclusion of a hygiene finish is particularly preferred where the personal hygiene product is an absorbent hygiene product, and inclusion of lanolin may be particularly preferred where the personal hygiene product is a nursing pad. However, it may be particularly preferable to include a phase change material to maintain a beneficial temperature for the skin in contact with the personal hygiene product. The use of such a phase change material in the personal hygiene product may have the added benefit of offering some physical relief to a user of the personal hygiene product where inflammation has already occurred and the skin in contact with the personal hygiene product feels hot and uncomfortable.

Optionally, the personal hygiene product may further comprise a solvent or diluent. This may act as a carrier for the present skin care additive and/or any other additives desirably provided to the personal hygiene product. The presence of a solvent or diluent may be particularly preferred when the diester skin care additive is applied to the pertinent layer of the personal hygiene product as a coating.

Optionally, the personal hygiene product may further comprise a stabiliser or emulsifier. Sorbitan fatty acid esters (e.g. Spans), their corresponding polyoxyethylene (POE) adducts (e.g. Tweens) and derivatives of hydrogenated castor oil (e.g. Crodurets) are particularly preferred stabilisers or emulsifiers for use in the present invention. A stabiliser may be present to assist in retaining the diester skin care benefit additive as an emulsion in a solvent, as this may assist in control of application to a pertinent layer of the personal hygiene care product during manufacture. The presence of a stabiliser is particularly preferred when the solvent (if present) is water. As such, the personal hygiene product may comprise an at least said first layer comprising a diester skin care additive, a solvent and a stabiliser.

Notwithstanding the comments made above, the diester skin care additive is preferably used neat, and so the presence of a solvent or diluent, and/or stabiliser or emulsifier is a less preferred embodiment.

Most suitably, the personal hygiene product at least first layer comprises a coating comprising the diester skin care additive, and in this case said coating is present on at least the top surface of the first layer. Alternatively, the diester skin care additive may be impregnated into the first layer, or incorporated in some other way, for example by mechanically embedding an encapsulated material containing the skin care additive into the at least first layer. However, providing the skin care additive as a coating applied to at least the top surface of the first layer of the personal hygiene product is preferred due to ease of manufacturing.

Additionally, the personal hygiene product said second layer may further comprise a coating comprising the skin care additive, and said coating is then present on at least the top surface of the second layer. This arrangement is particular preferred where the personal hygiene product is a wipe and both the first and second layer top surfaces may come in to contact with a user's skin.

Additionally, or alternatively, the personal hygiene product may further comprise a sealing means having a top surface and a bottom surface, and wherein said sealing means comprises a coating comprising the skin care additive, and said coating is present on at least the top surface of said sealing means. Such arrangement is particularly preferred where the hygiene product is a diaper, and the sealing means may be a leg cuff or waist band, preferable a leg cuff, which is also in contact with the user's skin to help to ensure non-leakage of urine and faeces. Leg cuffs in particular may inflict a high degree of abrasion on a user's skin when the user is moving around, and so the use of the diester skin care additive may be particularly desirable. The sealing means will have a laminar structure having a top and bottom surface, the top surface should be understood to be the skin contact surface when the personal hygiene product is in use, and the bottom surface in this case should be understood to be opposed to the skin contact surface. The sealing means is additional to the layered structure making up the body of the personal hygiene product, as described above.

Suitably, the personal hygiene product coating may be provided as a continuous or discontinuous layer. It may be preferable to provide the coating as a discontinuous layer so that the layer is permeable, such an embodiment will be preferred where the personal hygiene product is provided with an absorbent layer for the purpose of containment of bodily fluids such as urine, breast milk or menstrual discharge.

Suitably, the personal hygiene product comprises at least one layer formed from a textile. More preferably, the personal hygiene product may comprise at least one layer formed from a non-woven textile.

Additionally, or alternatively, the personal hygiene product may comprise at least one layer which is formed from paper pulp. Preferably, the paper pulp is derived from recycled paper pulp. Such an embodiment is preferred where the personal hygiene product is a diaper and the absorbent layer is formed from paper pulp, or alternatively where the personal hygiene product is a tissue, particularly a toilet tissue. One disadvantage identified by users of toilet tissue formed from recycled paper pulp is that the tissue has a rough feeling when used or abrades the skin more compared to virgin material alternatives; the diester skin care additive of the present invention provides an improved wet lubricancy which may alleviate a user's discomfort and render such a recycled paper pulp product more acceptable to a consumer.

In some particularly preferred embodiments, the personal hygiene product said second layer is an air permeable waterproof layer. This would be particularly preferred where the personal hygiene product is a diaper or a pad suitably provided with an absorbent layer for the purpose of containment of bodily fluids such as urine, breast milk or menstrual discharge. In this case, the second layer is not provided with the diester skin care additive. The use of a diester skin care additive in such a personal hygiene product finds particular utility, since the additive may advantageously provide both improved wet lubricancy and reduced skin irritancy effects. As such, preferably said personal hygiene product is a diaper or pad.

Methods of providing the skin care additive as a coating on at least the top surface of the at least first layer are also provided. A suitable method of providing a coating may be by means of a spray, roller, bar, blade, knife or foam application. Suitable apparatus for performing said coating methods are known to the skilled person and can be employed without technical difficulty.

Suitably the method includes providing the diester skin care additive containing coating in the form of a dispersion, emulsion or solution. The coating may also contain the additional materials mentioned above in relation to the diester skin care additive composition.

Optionally the method includes providing the diester skin care containing coating to the top surface of the at least second layer. Such a method is preferred where the personal hygiene product is a tissue or wipe.

Additionally, or alternatively, there is provided use of a personal hygiene product as described above to prevent or alleviate dermatitis. In particular, it is envisaged that use of a diaper as described above will allow for avoidance or reduction of nappy rash dermatitis: in this case the moist environment created from sweat and urine when the hygiene product is in use contributes to skin irritancy, and further the physical abrasion of the skin from contact with the top surface of the first layer of the product contributes to further skin damage or prevents healing. The personal hygiene product comprising the diester skin care additive of the present invention mitigates both of these negative contributing factors.

Additionally, or alternatively, there is provided use of a personal hygiene product described above to prevent or alleviate bed sores. In particular, it is envisaged that use of a pad as described above will allow for avoidance or reduction of bed sores due to the provision of wet lubricancy by the diester skin care additive in particular.

Furthermore, the use of a personal hygiene product as described above may desirably render a non-absorbent hygiene product product more comfortable of an end user, for example in the case of a tissue the perceived roughness of a product may be improved, and also user discomfort experienced during insertion of tampons may be advantageously reduced. This improved user comfort is the result of to the improved wet lubricancy of the personal hygiene product as provided by the diester skin care additive.

All of the features described herein may be combined with any of the above aspects, in any combination.

EXAMPLES

The present invention will now be described further by way of example only with reference to the following Examples and Figures, wherein:

FIG. 1 shows combined average TEWL of test panellists for SLS and example material, FIG. 2 shows combined average change in inflammation of test panellists as calculated using laser doppler, FIG. 3 shows the average dry and wet friction force at limit data obtained for a 15 gsm spunbond polypropylene textile sample, FIG. 4 shows the average dry and wet friction force at limit data obtained for a 15 gsm spunbond polypropylene textile sample, FIG. 5 shows the average dry and wet friction force at limit data obtained for a 10 gsm polypropylene textile sample, FIG. 6 shows the average dry and wet friction force at limit data obtained for a 10 gsm polypropylene textile sample, FIG. 7 shows the average dry and wet friction force at limit data obtained for a 10 gsm polypropylene textile sample with differing treat rates of example material.

FIG. 8 shows combined average TEWL of test panellists for a hygiene finish compared to hygiene finish plus example material and hygiene finish plus glycerine based emollient, FIG. 9 combined average TEWL of test panellists for a hygiene finish compared to hygiene finish plus example material and hygiene finish plus ester based emollient.

It will be understood that all tests and physical properties listed have been determined at atmospheric pressure and room temperature (i.e. about 20° C.), unless otherwise stated herein, or unless otherwise stated in the referenced test methods and procedures.

Example 1

Irritancy Reduction Testing

Textile Treatment 10 gsm polypropylene nonwoven textile was cut into 11 mm diameter circles. Each circle was individually treated with water based dispersions then dried to achieve either a treat rate of a) 1% sodium lauryl sulphate (SLS, Sample A) based on weight of textile, or b) 1% SLS and 2% di-PPG-2 myreth-10 adipate (a diester skin care additive in accordance with the present invention, Sample B) based on percentage by weight of textile. SLS is a known skin irritant, and so provides a good model for assessing skin irritancy in test subjects/panellists.

Irritation Panel Study

An irritation panel study was carried out, the study included 9 individual panellists. Each panellist was acclimatised to the laboratory environment at 20° C. and 45% relative humidity for 20 mins prior to the test, detailed below, being initiated.

For each panellist three test sites on each volar forearm were identified and marked (i.e. 6 test sites in total per panellist were assessed). An initial trans-epidermal water loss (TEWL) reading was taken using an AquaFlux AF200 Instrument to ensure no initial skin irritation at each of the 6 test sites.

Initial readings of inflammation were also taken with a laser doppler. Laser doppler readings are used to measure blood perfusion in the skin, and this is a measure of inflammation present in the skin at the test site. The laser doppler instrument measures the blood perfusion across the test area, and presents the data obtained via a heatmap of perfusion image. The instrument also assigns a value to each colour depicted in the heatmap of perfusion image and this allows a total irritation reading for the whole test area to be calculated and expressed as a numerical value.

For each panellist, three test circles of textile (prepared as detailed above), were applied to the skin under an occlusion patch, and then left for 24 hours. The same six test sites were used for each panellist, but the test material at each site was randomised between participants.

After 24 hours panellists were again acclimatised to the laboratory environment for 20 mins at 20° C. and 45% relative humidity. TEWL was measured using the POST (post occlusion stress test) protocol. Under this test the occlusion patch is removed, along with the textile sample, the test site is then wiped of any surface moisture, and then TEWL readings are taken immediately using the same AquaFlux AF200 Instrument. TEWL is measured until the water loss rate peaks, and for the following 5 minutes. Results are measured in total water loss for 5 minutes after water loss rate peaks. Once the TEWL readings were complete, laser doppler images were taken once again and compared to the initial readings.

In the panel test, as described above, Sample A is the textile with a finish of SLS at a treat rate of 1%, whereas Sample B is the textile with a finish containing 1% SLS and 2% diester skin care additive treat rate.

Example 2

Friction Reduction Testing

In this test two nonwoven textiles were tested 1) a 15 gsm spunbond polypropylene, and 2) a 10 gsm polypropylene. The nonwoven textile samples tested were coated with an emulsion containing either a) a commercially available hygiene finish product, or b) both a commercially available hygiene finish product and di-PPG-2 myreth-10 adipate a diester skin care additive in accordance with the present invention. Two commercially available hygiene finish products were utilised in the present tests, Stantex S 6757 (ex Pulcra) and Cirrasol Care (ex Croda) both provide a hydrophilic finish to nonwoven polypropylene textiles. Generally, such hygiene finish products are commonly applied to nonwoven textiles for use in absorbent personal hygiene products, to allow the rapid strikethrough of liquids through a skin contact textile layer to the underlying absorbent layer.

Skin friction measurements were taken using a polyolefin based synthetic skin substitute via a Lloyd LRX Tensile Tester. The synthetic skin was pulled over a 20 cm test strip of nonwoven textile, and the force at limit measured.

The nonwoven textile was left for a minimum of 24 hours in a temperature and humidity controlled environment at 22° C. and 50% relative humidity. Friction measurements were taken on the treated nonwoven textile in sets of 3 repeats per sample to be tested, and 3 samples were tested per treatment combination. Wet friction readings were made following taking the dry friction readings. Wet friction readings were made by wetting the textile sample to be tested with 0.2 g of deionised water, spread equally over the test piece using a fine mist spray. Three readings were then taken for each wet sample using the same procedure as the dry readings.

Figure 1:
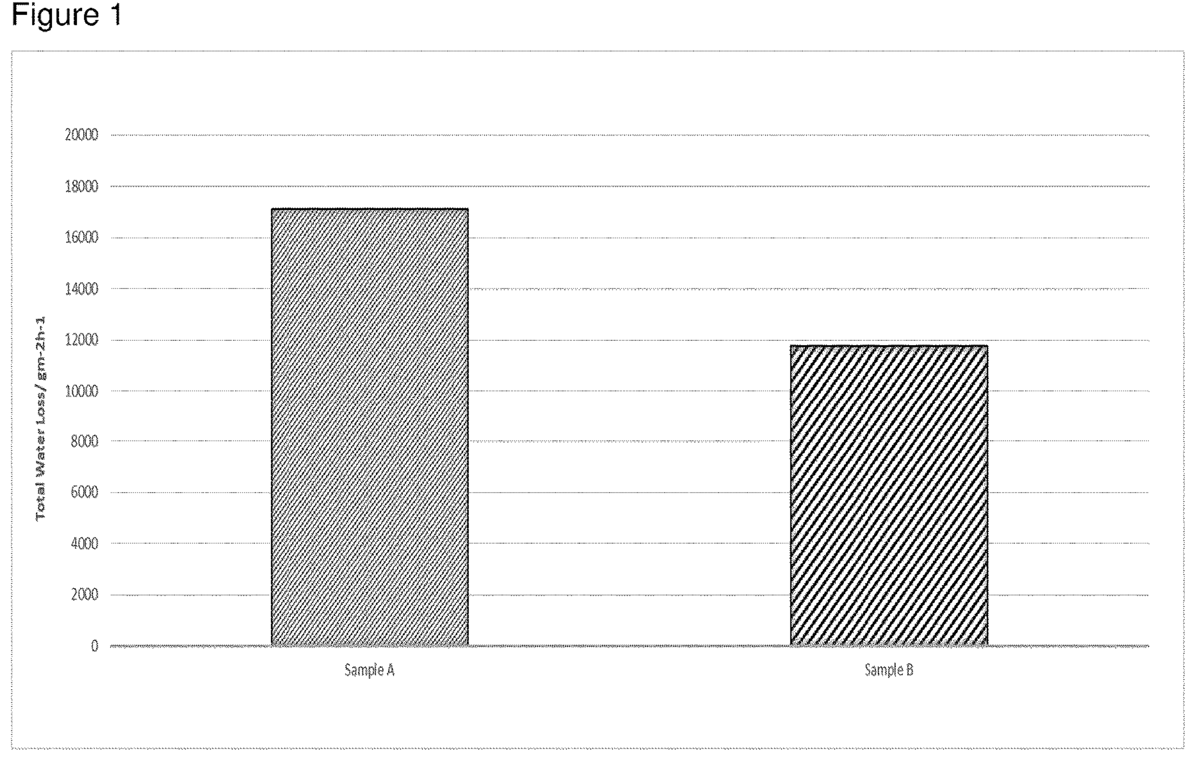
FIG. 1 shows the combined average TEWL of all panellists. The results obtained show a 31% decrease in skin water loss when using the diester skin care additive.
Figure 2:
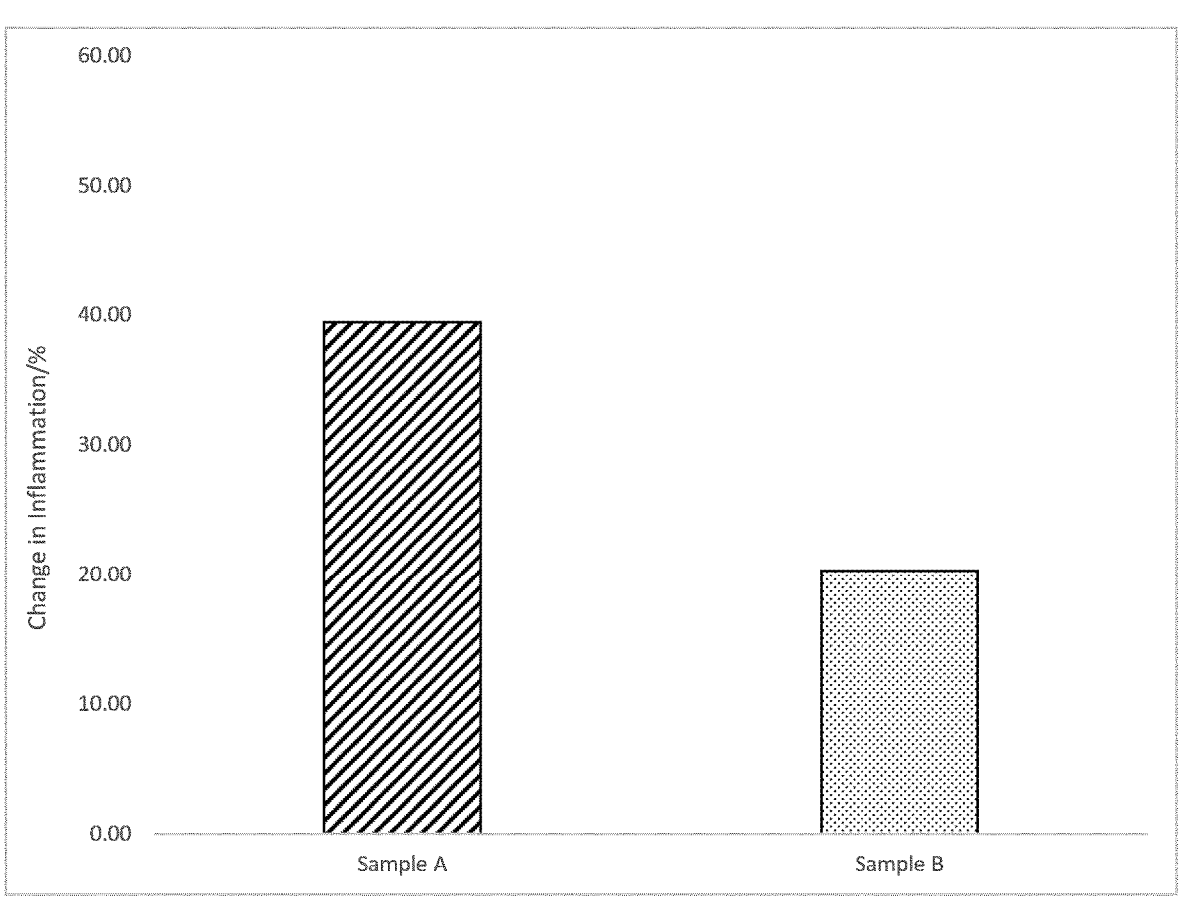
FIG. 2 shows the combined average change in inflammation of all panellists as calculated using laser doppler. The results obtained show a 49% reduction in inflammation for Sample B as compared to Sample A.
Figure 3:
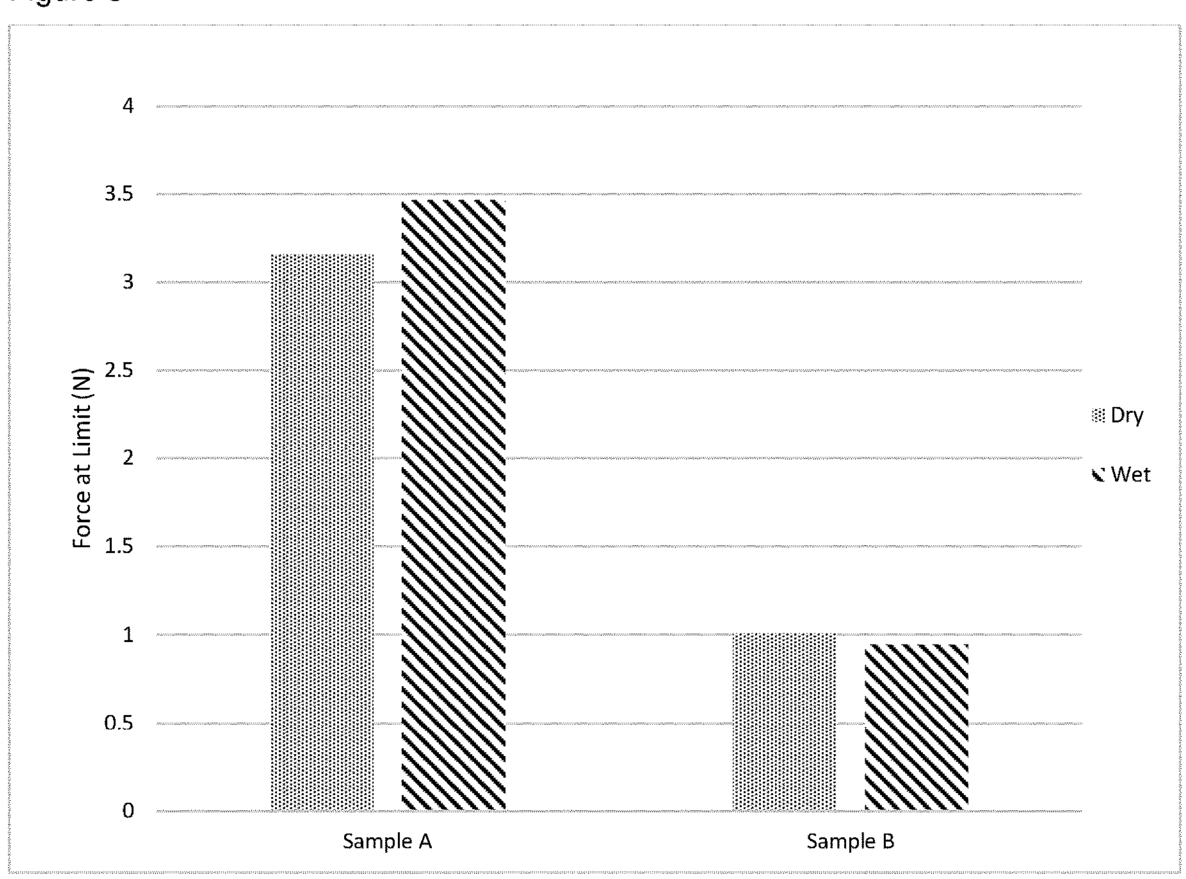

FIG. 3 shows the average dry and wet friction force at limit data obtained for a 15 gsm spunbond polypropylene textile sample, where Sample A is provided with a 0.5% Stantex S 6757 treat rate finish, and Sample B is provided with a 0.5% Stantex S 6757 and 2% diester skin care additive treat rate finish. Here it can be seen that Sample A exhibits a high skin friction and this skin friction is increased when the sample is wet. Sample B on the other hand shows a 68% lower skin friction when the textile sample is dry as compared to Sample A, and there is no increase/slight reduction in skin fiction when the sample is wet.

Figure 4:
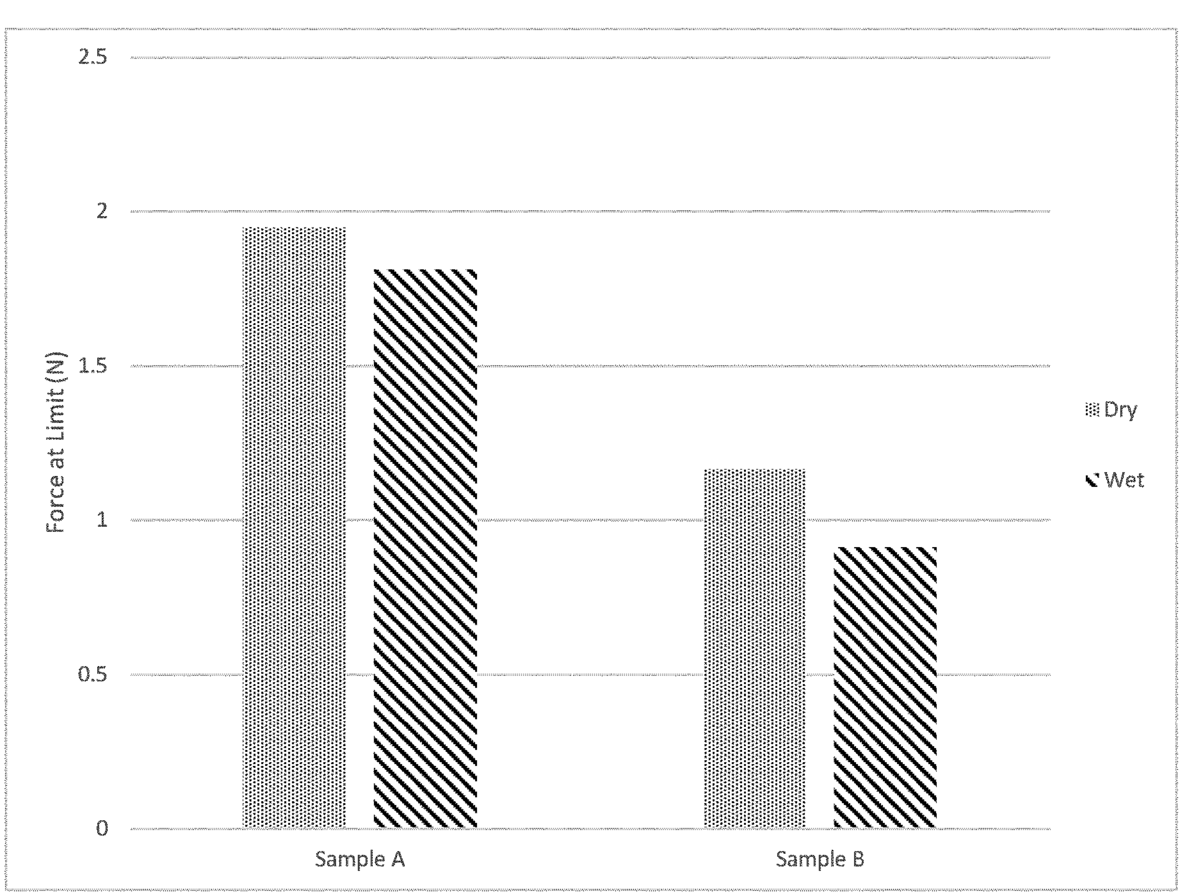

FIG. 4 shows the average dry and wet friction force at limit data obtained for a 15 gsm spunbond polypropylene textile sample, where Sample A is provided with a 0.5% Cirrasol Care treat rate finish, and Sample B is provided with a 0.5% Cirrasol Care and 2% diester skin care additive treat rate finish. Here it can be seen that Sample A exhibits a high skin friction and this skin friction is slightly decreased when the sample is wet. Sample B on the other hand shows a 36% lower skin friction when the textile sample is dry as compared to Sample A, and a further reduction in skin fiction when the sample is wet.

Figure 5:
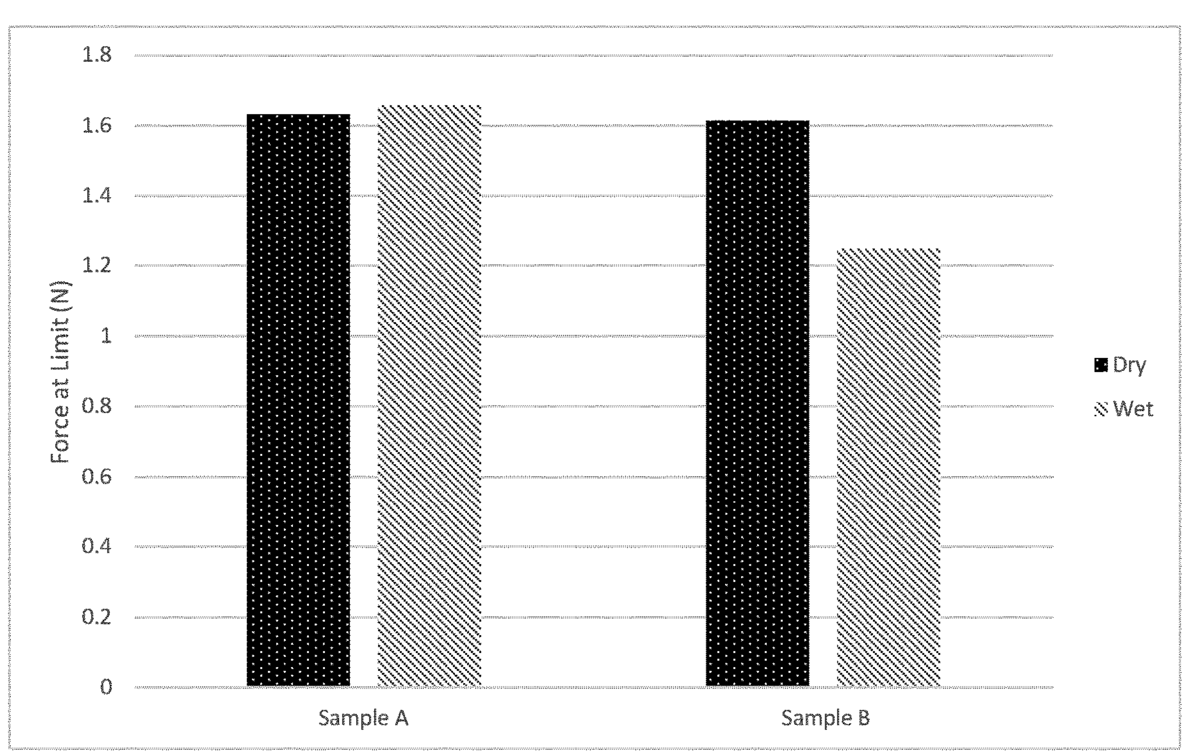

FIG. 5 shows the average dry and wet friction force at limit data obtained for a 10 gsm polypropylene textile sample, where Sample A is provided with a 0.5% Stantex S 6757 treat rate finish, and Sample B is provided with a 0.5% Stantex S 6757 and 2% diester skin care additive treat rate finish. For this textile sample, it can be seen that for Sample A a low skin friction when dry versus 15 gsm spunbond polypropylene textile is observed. However, this skin fiction is increased when the sample is wet. Although in this case Sample B provided no reduction in skin friction when the textile sample is dry as compared to Sample A, there is a significant reduction in skin fiction when the sample is wet.

Figure 6:
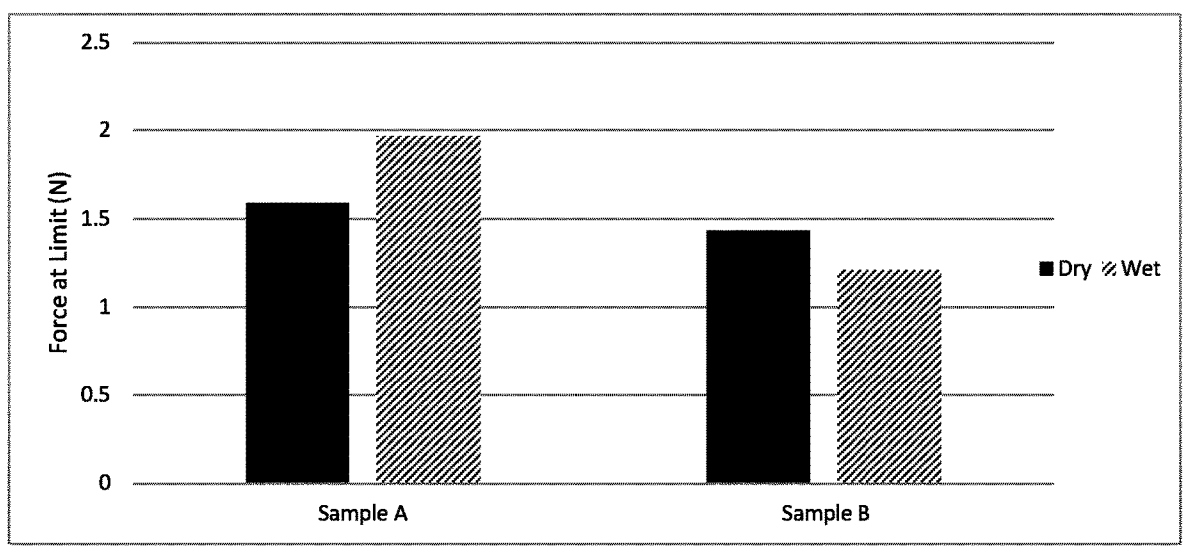

FIG. 6 shows the average dry and wet friction force at limit data obtained for a 10 gsm polypropylene textile sample, where Sample A is provided with a 0.5% Cirrasol Care treat rate finish, and Sample B is provided with a 0.5% Cirrasol Care and 2% diester skin care additive treat rate finish. Here it can be seen that Sample A has a relatively low dry skin friction, but this skin friction is increased when the sample is wet. For Sample B dry skin friction is reduced, and skin friction is further reduced when Sample B is wet.

Figure 7:
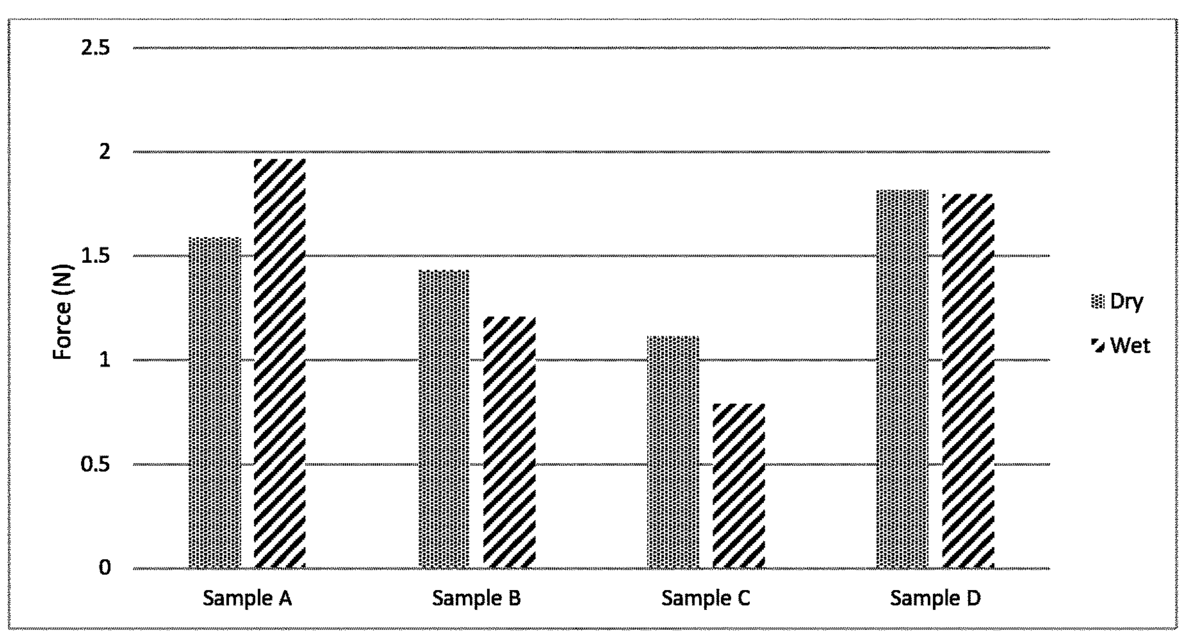

Different treat rates of the diester skin care additive were also tested as per the procedure outlined above. FIG. 7 shows the average dry and wet friction force at limit data obtained for a 10 gsm polypropylene textile sample, where Sample A is provided with a 0.5% Cirrasol Care treat rate finish, Sample B is provided with a 0.5% Cirrasol Care and 2% diester skin care additive treat rate finish, Sample C is provided with a 0.5% Cirrasol Care and 1% diester skin care additive treat rate finish, and Sample D is provided with a 0.5% Cirrasol Care and 0.5% diester skin care additive treat rate finish. Here it can be seen that the presence of the diester skin care additive at a treat rate of 1% and 2% reduce both wet and dry skin friction, with higher reductions observed for the wet samples. The presence of the diester skin care additive at a relatively low treat rate of 0.5% reduced the wet skin friction observed versus Sample A, but the dry skin friction was increased. Since wet friction is known to be a major contributing factor to skin damage in diaper use (in particular) it is believed that the increase in dry skin friction observed in this sample (which is still lower than that observed for the 15 gsm spunbond polypropylene textile sample with a Stantex S 6757 hygiene finish) could still offer a skin care benefit when in use.

Summary of Results

The above tests showed measurable reductions in irritation/inflammation from prolonged contact with a treated nonwoven textile when the nonwoven textile including the diester skin care additive at a treat rate of 2%. This was demonstrated in the reduction of water loss through the epidermis, indicating a less damaged skin barrier. The reduction in irritation was further demonstrated by reduced blood perfusion measured by laser doppler.

Further to the skin irritation/inflammation reduction, the same skin diester skin care additive can be used at 1% or 2% by weight treat rate on the nonwoven textile to give consistent reduction in wet friction, whilst also reducing or maintaining dry friction performance.

Example 3

Comparative Irritancy Reduction Testing vs. Glycerine Based Emollient

Textile Treatment 10 gsm polypropylene nonwoven textile was cut into 11 mm diameter circles. Each circle was individually treated with water based dispersions then dried to achieve a treat rate of a) 0.6% low-irritation hygiene finish (Cirrasol™ Care ex. Croda, Sample A), or b) 0.6% low irritation hygiene finish and 12% di-PPG-2 myreth-10 adipate (a diester skin care additive in accordance with the present invention, Sample B), or c) 0.6% low-irritation hygiene finish and 12% of a glycerine based emollient (Sample C). Treat rates are expressed as percentage by weight of textile.

Irritation Panel Study

An irritation panel study was carried out, the study included 16 individual panellists. Each panellist was acclimatised to the laboratory environment at 20° C. and 45% relative humidity for 20 mins prior to the test, detailed below, being initiated.

For each panellist three test sites on each volar forearm were identified and marked (i.e. 6 test sites in total per panellist were assessed). An initial trans-epidermal water loss (TEWL) reading was taken using an AquaFlux AF200 Instrument to ensure no initial skin irritation at each of the 6 test sites.

For each panellist, three test circles of textile (prepared as detailed above), were applied to the skin under an occlusion patch, and then left for 24 hours. The same six test sites were used for each panellist, but the test material at each site was randomised between participants.

After 24 hours panellists were again acclimatised to the laboratory environment for 20 mins at 20° C. and 45% relative humidity. TEWL was measured using the POST (post occlusion stress test) protocol. Under this test the occlusion patch is removed, along with the textile sample, the test site is then wiped of any surface moisture, and then TEWL readings are taken immediately using the same AquaFlux AF200 Instrument. TEWL is measured until the water loss rate peaks, and for the following 5 minutes. Results are measured in total water loss for 5 minutes after water loss rate peaks.

In the panel test, as described above, Sample A is the textile with a finish of only low-irritation hygiene finish at a treat rate of 0.6%, whereas Sample B is the textile with a finish containing 0.6% of the low-irritation hygiene finish and 12% diester skin care additive treat rate, and Sample C is the textile with a finish containing 0.6% of the low-irritation hygiene finish and 12% of a glycerine based emollient.

Figure 8:
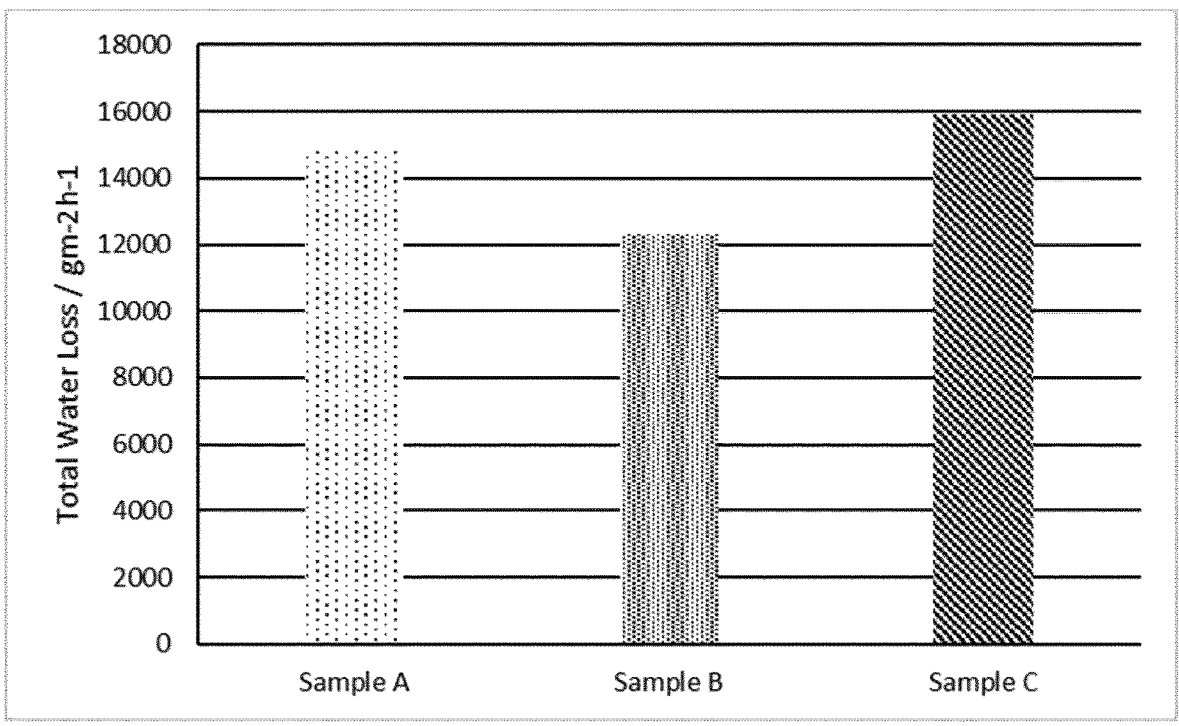

FIG. 8 shows the combined average TEWL of all panellists. The results obtained show, when compared to the low-irritancy hygiene finish alone, the diester skin care additive reduced skin irritation from nonwoven in contact with skin, while the glycerine based additive increased skin irritation.

Example 4

Comparative Irritancy Reduction Testing vs. Ester Based Emollient

Textile Treatment 10 gsm polypropylene nonwoven textile was cut into 11 mm diameter circles. Each circle was individually treated with water based dispersions then dried to achieve a treat rate of a) 0.6% low-irritation hygiene finish (Cirrasol™ Care ex. Croda, Sample A) based on weight of textile, or b) 0.6% low-irritation hygiene finish and 12% di-PPG-2 myreth-10 adipate (a diester skin care additive in accordance with the present invention, Sample B), or c) 0.6% low-irritation hygiene finish and 12% of a saturated tri-ester based emollient (Crodamol™ GTCC ex. Croda, Sample C). Treat rates are expressed as percentage by weight of textile.

Irritation Panel Study

An irritation panel study was carried out, the study included 16 individual panellists. Each panellist was acclimatised to the laboratory environment at 20° C. and 45% relative humidity for 20 mins prior to the test, detailed below, being initiated.

For each panellist three test sites on each volar forearm were identified and marked (i.e. 6 test sites in total per panellist were assessed). An initial trans-epidermal water loss (TEWL) reading was taken using an AquaFlux AF200 Instrument to ensure no initial skin irritation at each of the 6 test sites.

For each panellist, three test circles of textile (prepared as detailed above), were applied to the skin under an occlusion patch, and then left for 24 hours. The same six test sites were used for each panellist, but the test material at each site was randomised between participants.

After 24 hours panellists were again acclimatised to the laboratory environment for 20 mins at 20° C. and 45% relative humidity. TEWL was measured using the POST (post occlusion stress test) protocol. Under this test the occlusion patch is removed, along with the textile sample, the test site is then wiped of any surface moisture, and then TEWL readings are taken immediately using the same AquaFlux AF200 Instrument. TEWL is measured until the water loss rate peaks, and for the following 5 minutes. Results are measured in total water loss for 5 minutes after water loss rate peaks.

In the panel test, as described above, Sample A is the textile with a finish of only low-irritation hygiene finish at a treat rate of 0.6%, whereas Sample B is the textile with a finish containing 0.6% of the low-irritation hygiene finish and 12% diester skin care additive, and Sample C is the textile with a finish containing 0.6% of the low-irritation hygiene finish and 12% of a saturated tri-ester based emollient.

Figure 9:
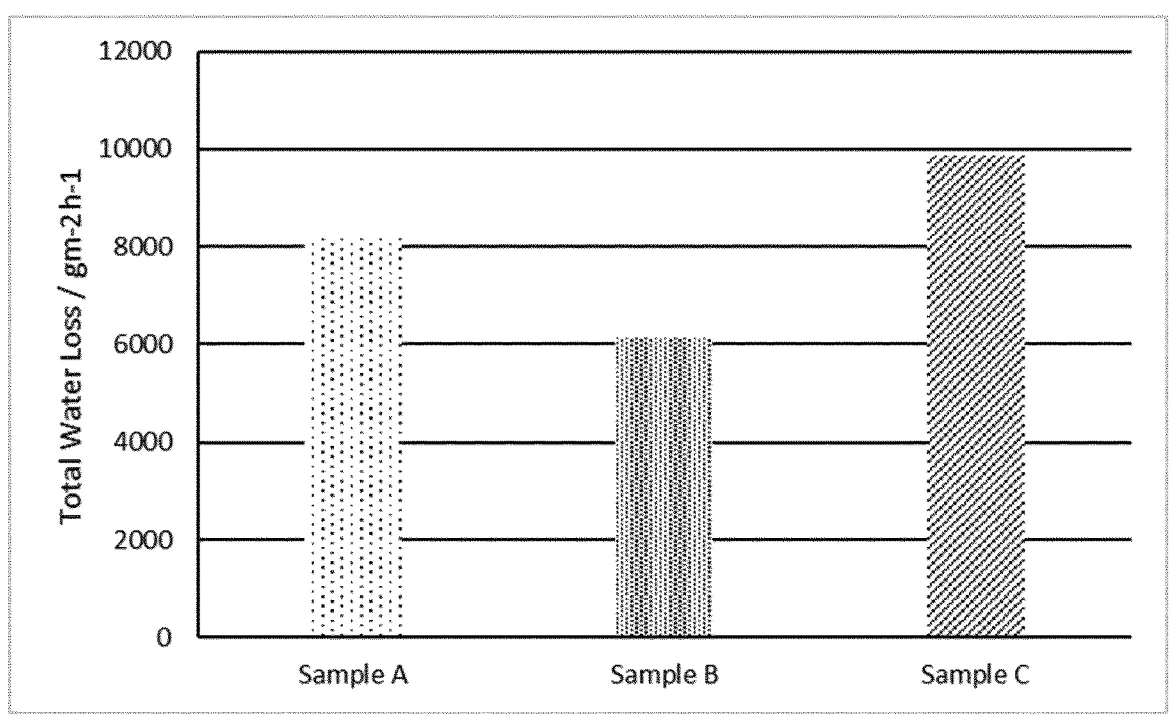

FIG. 9 shows the combined average TEWL of all panellists. The results obtained show, when compared to the low-irritancy hygiene finish alone, the diester skin care additive reduced skin irritation from nonwoven in contact with skin, while the tri-ester based additive increased skin irritation.

The invention claimed is:

1. A personal hygiene product comprising at least a first layer having a top surface and a bottom surface, wherein at least the first layer comprises a skin care additive, wherein the skin care additive is a diester which is di-PPG-2 myreth-10 adipate, wherein the personal hygiene product is not wetted before application to the skin, wherein the diester skin care additive is present in an amount of between 1 weight % and 2 weight % relative to the layer(s) containing the diester skin care additive, and wherein the at least first layer is formed from a nonwoven textile.

2. The personal hygiene product according to claim 1, further comprising at least a second layer having a top surface and a bottom surface.

3. The personal hygiene product according to claim 1, further comprising a solvent or diluent.

4. The personal hygiene product according to claim 1, further comprising an additional additive.

5. The personal hygiene product according to claim 1, further comprising a stabiliser.

6. The personal hygiene product according to claim 1, wherein the skin care additive is present on at least the top surface of the first layer.

7. The personal hygiene product according to claim 2, wherein the skin care additive is present on at least the top surface of the second layer.

8. The personal hygiene product according to claim 1, wherein the personal hygiene product further comprises a sealing means having a top surface and a bottom surface, and wherein the sealing means comprises a coating comprising the skin care additive, and the coating is present on at least the top surface of the sealing means.

9. The personal hygiene product according to claim 2, further comprising at least one absorbent layer interposed between the first layer and the second layer, such that the personal hygiene product is an absorbent hygiene product.

10. The personal hygiene product according to claim 2, wherein the second layer is an air permeable waterproof layer.

11. The personal hygiene product according to claim 1, wherein the personal hygiene product is a diaper or pad.

12. The personal hygiene product according to claim 1, wherein skin exposed to the personal hygiene product for a 24-hour period showed a reduction in skin friction compared to a personal hygiene product not containing the skin care additive di-PPG-2-myreth-10 adipate.

13. The personal hygiene product according to claim 1, wherein skin exposed to the personal hygiene product for a 24-hour period showed a reduction in trans-epidermal water loss (TEWL) compared to a personal hygiene product not containing the skin care additive di-PPG-2-myreth-10 adipate.

14. The personal hygiene product according to claim 1, wherein the personal hygiene product is in a dry state when applied to the skin.

15. The personal hygiene product according to claim 1, wherein the personal hygiene product is in prolonged contact with the skin.

16. A method to prevent or alleviate dermatitis, comprising administering to a subject in need thereof the personal hygiene product according to claim 1.

17. A method to prevent or alleviate bed sores, comprising administering to a subject in need thereof the personal hygiene product according to claim 1.

* * * * *